(12) United States Patent
Johansson et al.

(10) Patent No.: US 8,267,571 B2
(45) Date of Patent: Sep. 18, 2012

(54) MIXING SYSTEM AND MIXING METHOD FOR MEDICAL PURPOSES

(75) Inventors: Erik Johansson, Uppsala (SE); Niklas Axen, Järlasa (SE); Staffan Bowald, Fjärdhundra (SE); Sven Olerud, Länna (SE); Hans Jacobsen, Täby (SE)

(73) Assignee: OrtoWay AB, Djursholm (SE)

( * ) Notice: Subject to any disclaimer, the term of this patent is extended or adjusted under 35 U.S.C. 154(b) by 657 days.

(21) Appl. No.: 12/384,805

(22) Filed: Apr. 8, 2009

(65) Prior Publication Data

US 2009/0266420 A1    Oct. 29, 2009

Related U.S. Application Data

(63) Continuation of application No. PCT/SE2008/000552, filed on Oct. 10, 2008.

(30) Foreign Application Priority Data

Oct. 10, 2007 (SE) ...................................... 0702267

(51) Int. Cl.
*B01F 3/12* (2006.01)
*B01F 13/06* (2006.01)
*B01F 11/00* (2006.01)
*B01F 15/02* (2006.01)

(52) U.S. Cl. ......... 366/139; 366/189; 366/195; 366/332

(58) Field of Classification Search ................... 366/139, 366/189, 163.1, 191, 267, 268, 269, 195, 366/332; 604/88
See application file for complete search history.

(56) References Cited

U.S. PATENT DOCUMENTS

| | | | | |
|---|---|---|---|---|
| 1,718,603 A | * | 6/1929 | Smith | 604/206 |
| 3,164,303 A | * | 1/1965 | Trautmann | 222/190 |
| 3,343,817 A | * | 9/1967 | Carangelo et al. | 366/314 |
| 4,516,967 A | * | 5/1985 | Kopfer | 604/87 |
| 4,676,406 A | | 6/1987 | Frischmann et al. | |

(Continued)

FOREIGN PATENT DOCUMENTS

CH     541 481 A     9/1973

(Continued)

OTHER PUBLICATIONS

International Search Report date of mailing Mar. 30, 2005 for International Application No. PCT/NL2004/000827.

*Primary Examiner* — Tony G Soohoo
(74) *Attorney, Agent, or Firm* — Mintz Levin Cohn Ferris Glovsky and Popeo, P.C.

(57) ABSTRACT

A system and a method for making an injectable mixture using at least one first pulverulent component and a second liquid component with a first piston/cylinder arrangement with a cylinder with an axial extension and a piston, wherein the cylinder includes a measured amount of the pulverulent component, a separate reservoir including a corresponding measured amount of the liquid component, and a transfer device for sealed transfer of said amount of the liquid component to the cylinder for subsequent mixing and injection of the completed mixture. The first piston/cylinder arrangement is an injection syringe. A mixing element being manoeuvrable by a user is positioned inside the cylinder. At least one gas transferring channel means leading to the cylinder is arranged at the cylinder. Engagement means are arranged for connecting the first injection syringe to the separate reservoir during transfer of the liquid component.

24 Claims, 15 Drawing Sheets

U.S. PATENT DOCUMENTS

| | | | | |
|---|---|---|---|---|
| 4,808,184 A * | 2/1989 | Tepic | | 604/518 |
| 4,889,432 A * | 12/1989 | Patterson | | 366/139 |
| 5,181,918 A * | 1/1993 | Brandhorst et al. | | 606/92 |
| 5,252,301 A | 10/1993 | Nilson et al. | | |
| 5,435,645 A | 7/1995 | Facciol et al. | | |
| 5,549,380 A | 8/1996 | Lidgren et al. | | |
| 5,551,778 A | 9/1996 | Hauke et al. | | |
| 5,636,921 A * | 6/1997 | Murata et al. | | 366/105 |
| 5,779,356 A * | 7/1998 | Chan | | 366/139 |
| 5,788,463 A * | 8/1998 | Chan | | 417/63 |
| 5,951,160 A * | 9/1999 | Ronk | | 366/130 |
| 5,957,166 A * | 9/1999 | Safabash | | 141/26 |
| 6,017,349 A | 1/2000 | Heller et al. | | |
| 6,120,174 A * | 9/2000 | Hoag et al. | | 366/139 |
| 6,478,788 B1 * | 11/2002 | Aneas | | 604/411 |
| 7,073,936 B1 * | 7/2006 | Jonsson | | 366/139 |
| 8,038,962 B2 * | 10/2011 | Hoerger et al. | | 422/263 |
| 2001/0021820 A1 | 9/2001 | Lynn | | |
| 2003/0086332 A1 * | 5/2003 | Jonsson | | 366/139 |
| 2006/0164913 A1 * | 7/2006 | Arramon | | 366/139 |
| 2008/0214998 A1 * | 9/2008 | Kurek et al. | | 604/93.01 |
| 2009/0266420 A1 * | 10/2009 | Johansson et al. | | 137/1 |

FOREIGN PATENT DOCUMENTS

| | | |
|---|---|---|
| WO | WO 2005/053581 A1 | 6/2005 |

* cited by examiner

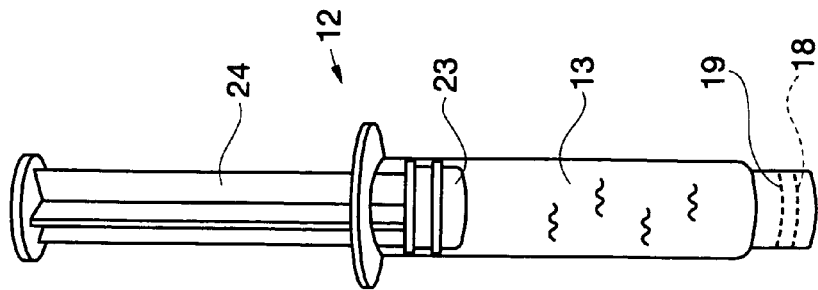
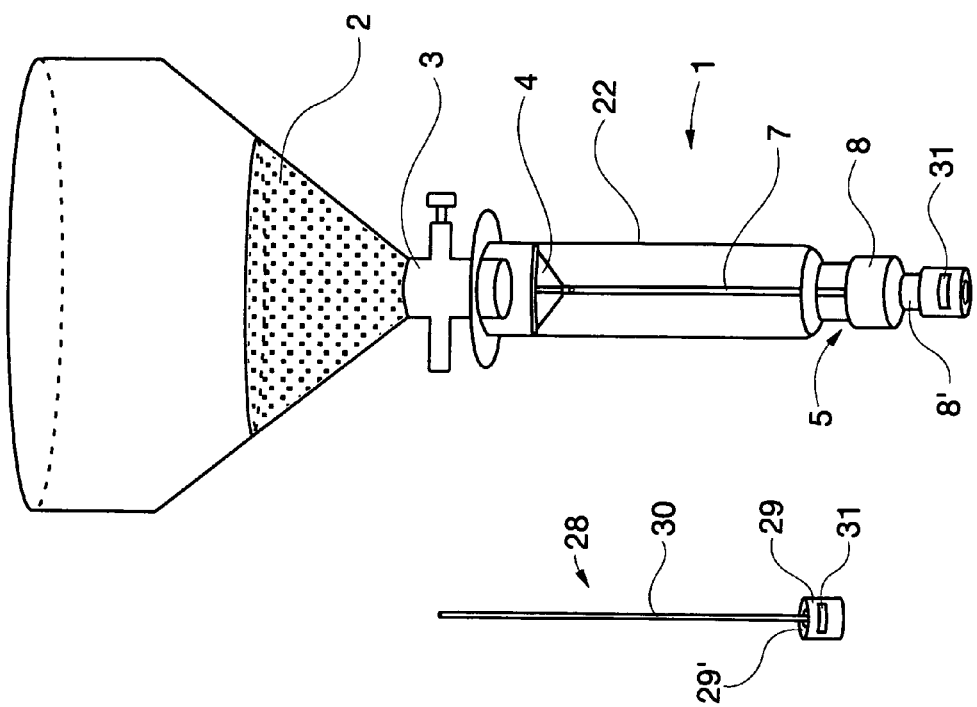
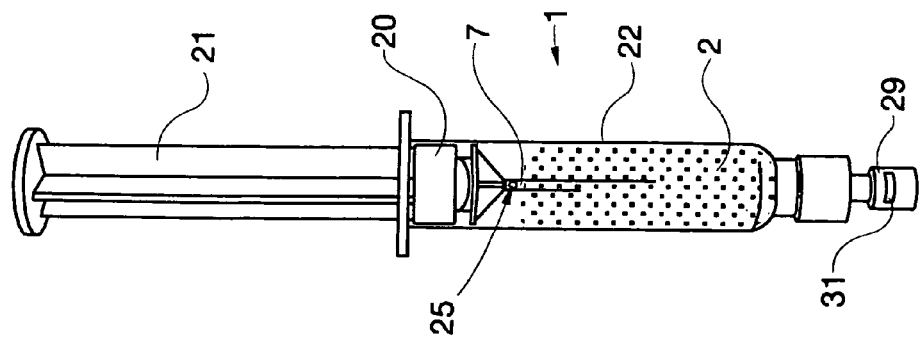

US 8,267,571 B2

MIXING SYSTEM AND MIXING METHOD FOR MEDICAL PURPOSES

CROSS-REFERENCE TO RELATED APPLICATIONS

This application is a continuation application of International Application PCT/SE2008/000552, filed on Oct. 10, 2008, which claims priority to SE 0702267-6, filed on Oct. 10, 2007, the disclosures of which are incorporated herein by reference in their entirety.

FIELD OF THE INVENTION

Systems and methods for making an injectable mixture for medical purposes using at least one pulverulent component and one liquid component are provided.

BACKGROUND OF THE INVENTION

It is previously known to introduce different paste-like materials into the human body for medical and in particular orthopaedic purposes. Such materials are often called bone cement, bone replacement material or "bone grafts" (hereinafter referred to as "bone cement"). These material can be of different types, for example based on synthetic or ceramic material and be used for filling voids in bone tissue or for supporting fastening of implants on bone tissue.

A known bone cement is based on settable synthetic material, in particular an acrylic plastic—polymethylmetacrylate (PMMA), which is commonly used in different orthopaedic applications. Traditionally bone cement is used in hip joints and in knee joints but lately also for filling voids in vertebrae, in wrists and more applications. The bone cement may be a two-component material wherein the starting materials are comprised of one pulverulent component and one liquid component, which have to be thoroughly mixed in accurately measured amounts for obtaining a good result.

It is known that the hardening is relatively fast and during heat release, which later escalates the hardening process, which is the reason that it is important that the process of mixing and application of the bone cement is relatively fast in order not to jeopardize quality of the result.

At present mixing is often undertaken by providing measured amounts of the two components into a mixing bowl wherein mixing is obtained through manual agitation.

Thereupon the mixture is transferred over a funnel and a supply pipe to an injection device including a piston cylinder unit.

In respect of this technology, strict requirements for sterility of the bone cement can be difficult to withhold during such preparation. Toxic vapours resulting from the components also are a risk factor for a person handling the material.

In another common arrangement, pulverulent and liquid components are provided separately to a mixing device wherein a mechanical mixer provides the agitation.

Background art includes U.S. Pat. No. 5,435,645 and WO 2005/053581.

SUMMARY OF THE INVENTION

It is an aim of the present invention to provide a system and a method as above which address above problems in the direction of at least mitigating them.

This is achieved in respect of the system according to above through the features disclosed herein.

Hereby is achieved that a system is created which is simple to handle for a user, and which is suitable for larger as well as very small mixture amounts, for example very small amounts of bone cement, as example about 1-20 ml, for precision application in narrow cavities in connection with open surgery as well as minimally-invasive surgery.

The system is, however, also suitable for use in respect of greater amounts of bone cement as well as other types of mixtures for medical purposes. By providing a mixing element ensures the possibility of adequate and thorough mixing and thereby high quality of the mixture. By providing a gas transferring channel means, a possibility is obtained on the one hand for de-aerating the completed mixture, and on the other hand to supply a sterilizing gas to the pulverulent component.

The first injection syringe and the separate reservoir can be connected or "docked" in connection with the transfer of the liquid component. Hereby is guaranteed that the closed transfer is safe and according to high hygienic requirements at the same time as the different components, the first injection syringe and the second piston/cylinder arrangement, can be handled separately and be treated in such ways that are suitable for the different components.

Hereby can be mentioned that the two components of some bone cements, such as for example today's PMMA-based cement, can not be sterilized with the same method, because one method which is suitable for one component can be ineffective or harmful for the other component. For that reason it is important that a system that can be used for a plurality of different cements on the market has separate containers for the different component so that the system gives the possibility of applying different sterilizing methods when used for bone cements where it is necessary.

Concerning bone cements of the mentioned kind, the liquid component has generally one commercially and technically applied sterilizing method which is aseptic filling over a sterile filter. The pulverulent component can be gas sterilized (ETO) or be sterilized through radiation. During gas sterilization, a pulverulent component which is pre-filled and inside a package for a packed syringe inside a package of a material which is permeable to the sterilizing gas but micro biologically tight is subjected to an atmosphere with this sterilizing gas. The gas can thus penetrate a package material, reach the syringe and subsequently reach and sterilize the pulverulent component through the gas transferring channel means. In practice, the packaged syringe is put inside a kind of a gas vessel, wherein for example is created an underpressure, whereupon supplied sterilizing gas is sucked into the syringe and thereby the pulverulent component over said gas transferring channel means. After completed gas treatment, the gas is sucked out from the package over the same channel means and through the package material.

By the gas transferring channel means being displaceably arranged inside the cylinder and in particular a mouth of the gas transferring channel means being displaceable in the axial direction of the cylinder, very effective de-aerating of the mixture after completed mixing is possible. During mixing, air enclosures are created inside the mixture, which could seriously deteriorate the quality of the mixture/bone cement or the like. Bone cement is namely often relatively highly viscous and air enclosures can therefore not simply be shaken or pressed out in an effective manner. Through this aspect of the invention, however, a gas transferring channel means can be brought to "search" for these air enclosures through its displacement inside the cylinder, normally during simultaneous activation of the first injection syringe, such that a minor over-pressure prevails therein. Considerably more effective de-aeration of the complete mixture body can therefore be achieved through the invention.

The invention is particularly suited for preparing paste-like mixtures, wherein it's usual that the air enclosures remain in the completed paste. The invention has, however, also its application for other mixtures wherein air bubbles easily become more permanently remaining after completed mixing procedure. It can be in respect of somewhat jelly-like or syrupy mixtures.

By the separate reservoir being included in a second piston/cylinder arrangement and in particular in a second injection syringe, standard components can be used, which are easy to handle and economically advantageous. Through this arrangement it is possible to introduce a very precise amount of the liquid component into the cylinder such that high quality can be reached for the mixture.

By the second engagement means being releasable, the first injection syringe can be freed from the second piston cylinder arrangement after completed transfer of liquid component for further handling of the completed mixture. It is rational and preferred that a means for manoeuvring the mixing element also includes said gas transferring means. Hereby it is achieved in a simple manner that these functions are integrated and hereby the possibility of de-aerating according to the above is simplified.

It is preferred also that said gas transferring channel means is comprised of a transfer channel means for transferring the liquid component from the second piston/cylinder arrangement, whereby further integration of different functions into the system is achieved.

It is also preferred that a means for manoeuvring the mixing element includes said transfer channel means.

In the cases where the first, and on occasion the second, injection syringe are single use articles the problems with cleaning and reusing of these details are avoided and in case they are comprised of standard components, an economically advantageous solution is obtained.

It is thus preferred that the system is adapted for use in connection with the application of bone cement into a patient, but also use within other medical applications are envisaged such as for medical mixtures with the property that they bind air enclosures and therefore should be de-aerated before being administered.

The corresponding advantages are obtained in respect of a method according to the invention.

BRIEF DESCRIPTION OF THE DRAWINGS

The invention shall now be described in more detail by way of embodiments and with reference to the annexed drawings.

FIGS. 1a-c show different steps for filling and sterilizing a pulverulent component into a first injection syringe.

FIG. 1d shows a free holder means in the form a needle shaped element.

FIGS. 2a and 2b show two steps in connection with filling a liquid component into a second injection syringe.

DETAILED DESCRIPTION OF THE EMBODIMENTS

Figure 1C:
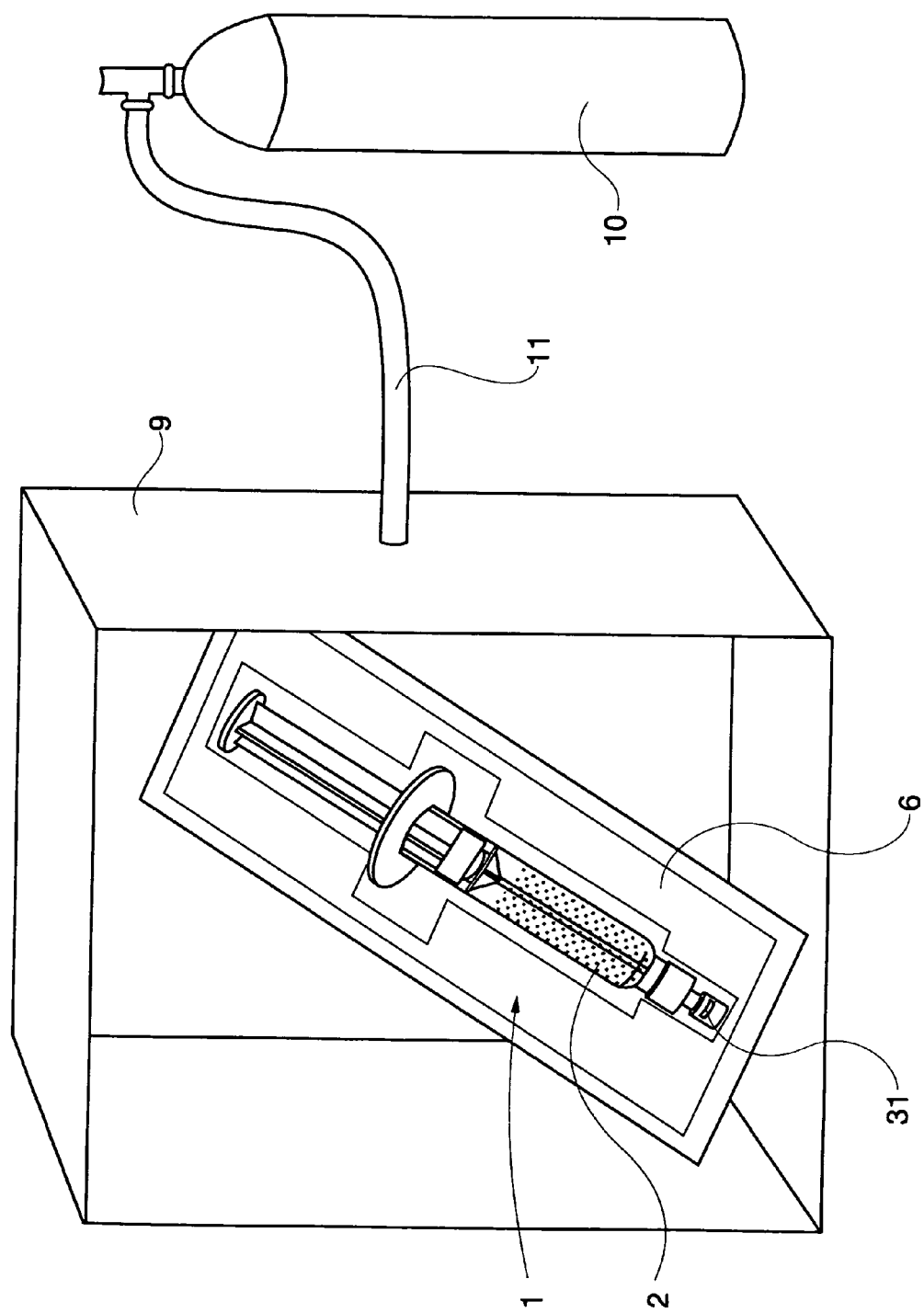

Like and similar elements in the different embodiments have been given the same reference numerals.

With reference to FIGS. 1a-1c the process of sterilizing a pulverulent component 2 inside the first injection syringe 1 is shown. In FIG. 1a is diagrammatically shown a first filling station, whereby a dosing and filling device 3 is arranged to deliver a measured amount of the pulverulent component 2, which falls down into a cylinder 2 of the first injection syringe 1.

First injection syringe 1 is also provided with a mixing element 4 which is connected to a manoeuvring means 7-8 for making it possible to rotate the mixing element 4 and to make it possible to displace it in an axial direction of the cylinder during a later mixing operation.

A tubular portion 7 of the manoeuvring means 7-8 having an inside channel extends from the mixing element 4 through a passage (not shown) in a connection portion 5, to a first engagement means in the form of an outside thread on a rotation portion 8. The connection portion 5 has an outer male thread (not shown) for later application of a chosen injection needle when the completed mixture is to be injected.

From FIG. 1d shows a free holding means 28 in the form of a needle-shaped element 30, which is rigidly connected to a fastening element in the form of a sleeve-shaped element 29, which has means such as inside female threads 29' for co-operation with corresponding fastening means such as the above-mentioned male threads on the connection portion 5. Also other fastening principals can be envisaged such as bayonet connection means.

The aim of the free holding means 28 is that after filling with pulverulent component 2 and until the point where mixing of the two components is to be made, prevent the pulverulent component 2 from penetrating into the channel inside the tubular portion 7, which otherwise could risk blocking the latter for gas transfer and later transferring of a liquid component. In the embodiment shown in FIG. 1d, the needle-shaped element 30 of the free holding means 28 is hollow all over its length and together with the sleeve shaped element 29, which has a recess 31, there is formed a gas penetrable connection through the free holding means 28 such that gas can penetrate from the outside to the inside of the first injection syringe 1 for sterilizing purposes. Certain gas transfer can also be had between the envelop surface of the needle-shaped element 30 and the channel wall of the tubular portion 7.

In FIG. 1b is shown in a second stage that a piston 20 with a piston rod 21 for its manoeuvring is introduced into the free end of the cylinder of the first injection syringe 1, which is filled with pulverulent component 2 for forming a first piston/cylinder arrangement.

In FIG. 1c is shown in a third stage the first injection syringe 1, filled with pulverulent component 2, is placed in a chamber 9, which is arranged from a gas container 10 over a gas conduit 11 to feed a sterilizing gas into the chamber 9 enclosing a package with the first injection syringe 1. With reference to the above, sterilizing gas can thus penetrate into the inside of the first injection syringe 1 over, to start with, the recess 31. After completed sterilization, the first injection syringe 1 is ready for delivery/use. It should be noted that other solutions for achieving gas transfer is within the scope of the invention such as for example that all gas transfer is between an envelope surface of a non-hollow needle-shaped element 30 and the channel wall of the tubular portion 7.

Also other per se known sterilizing methods for different uses of the invention are within the scope of the invention. It is thus possible to use radiation sterilization with ionizing radiation or for example certain electromagnetic radiation with sufficient power for the purpose. It is also possible to use heating in dry heat or dry heat atmosphere in certain instances.

Figure 2A:
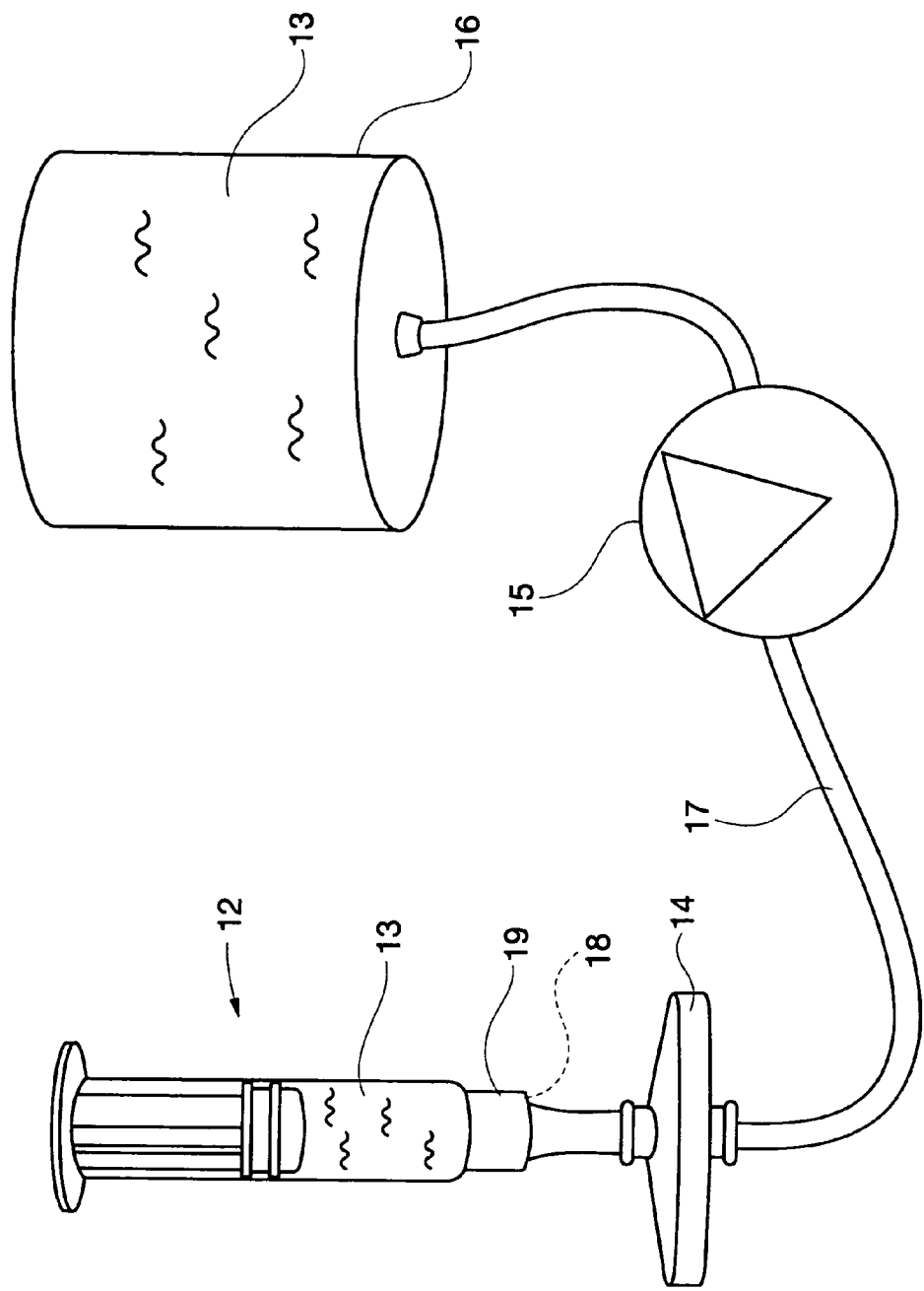

In FIG. 2a is shown a first stage for filling a liquid component 13 into a second injection syringe 12. Hereby is in a corresponding manner as during filling of the first injection syringe 1, the second injection syringe 12 arranged for receiving a measured amount of the liquid component 13 contained inside a supply 16 over a feed pump 15, which is arranged to provide the inside of the second injection syringe 12 with said measured amount of the liquid component over a liquid conduit 17 and a sterile filter 14.

On the lower part of the second injection syringe, as shown in FIG. 2a, is arranged a closure 19 with second engagement means 18 in the form of a inner thread (not shown) or the like.

In FIG. 2b is shown in a second stage where the filled second injection syringe 12 has been provided with the piston 23 with associated piston rod 24 for manoeuvring of the piston. After completed sterilization outside with a sterilizing gas, possibly when being packaged inside a gas penetrable plastic bag (not shown), the second injection syringe is ready for delivery/use.

It should be mentioned that other sterilizing methods for the liquid component are within the scope of the invention. Thus, depending on the material to sterilize, other per se known methods can be used such as radiation, sterilization with ionizing radiation or for example certain electromagnetic radiation with sufficient power for the application. Also for example autoclaving in moist heat can be used for certain applications.

In FIGS. 3a-f are shown a sequence for conducting the mixing of the two components for achieving of an injectable mixture of, in the shown example, bone cement.

Figure 3A:
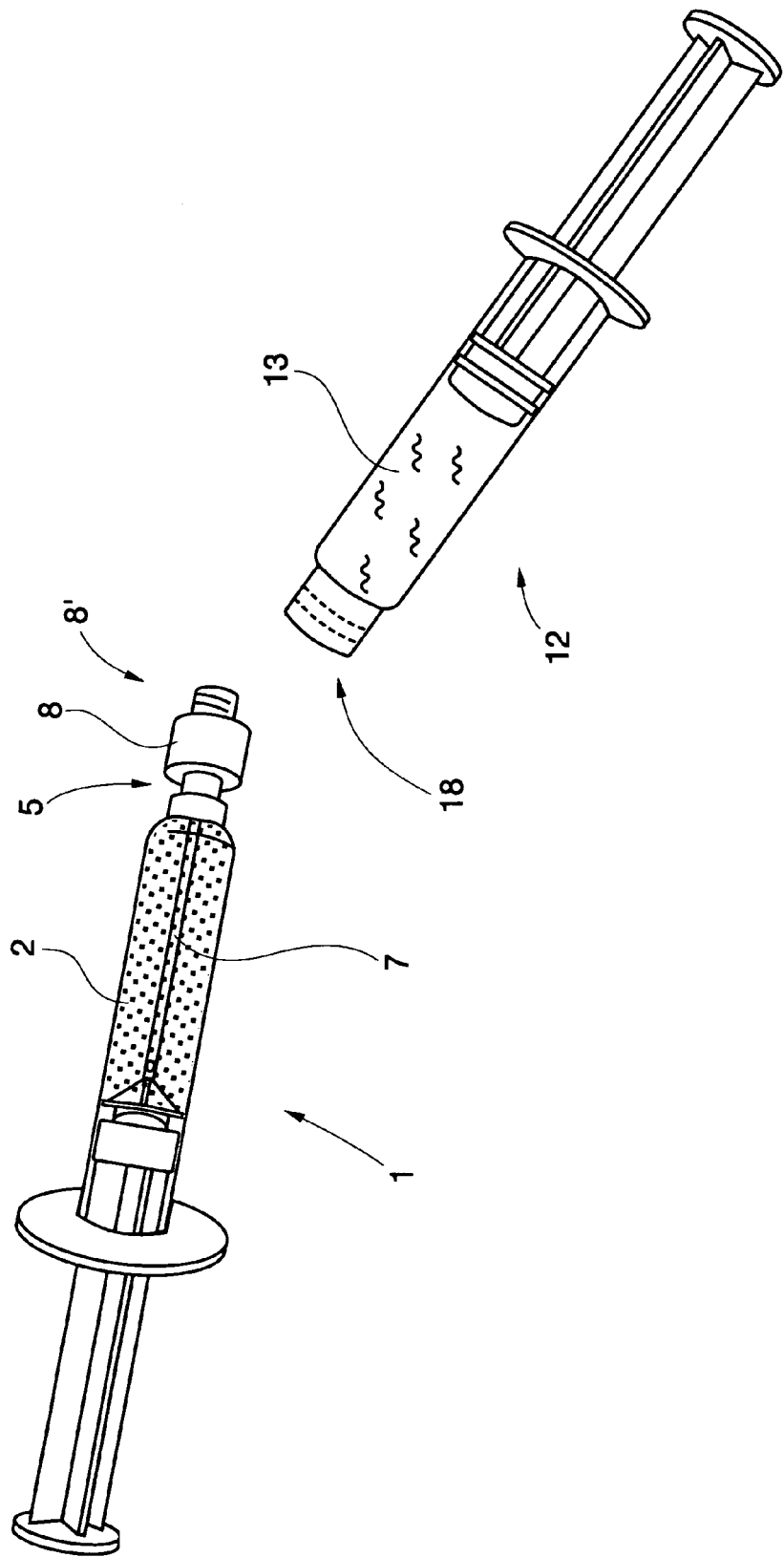
FIGS. 3a-f show different steps in connection with mixing components before application of the mixture.

FIG. 3a shows the first 1 and the second 12 injection syringe taken out from their sterile packages and prepared for being connected through the first and second engagement means 8' and 18, respectively. These are here in the form of an outside thread 8' outermost at the rotational portion 8 as concerns the first injection syringe 1 and said inner thread at 18 as concerns the second injection syringe 12. The free holding means 28 shown in FIG. 1d has already been removed from the first injection syringe 1 and left the channel inside the manoeuvring means 7-8 open for introduction of the liquid component 13.

Figure 3B:
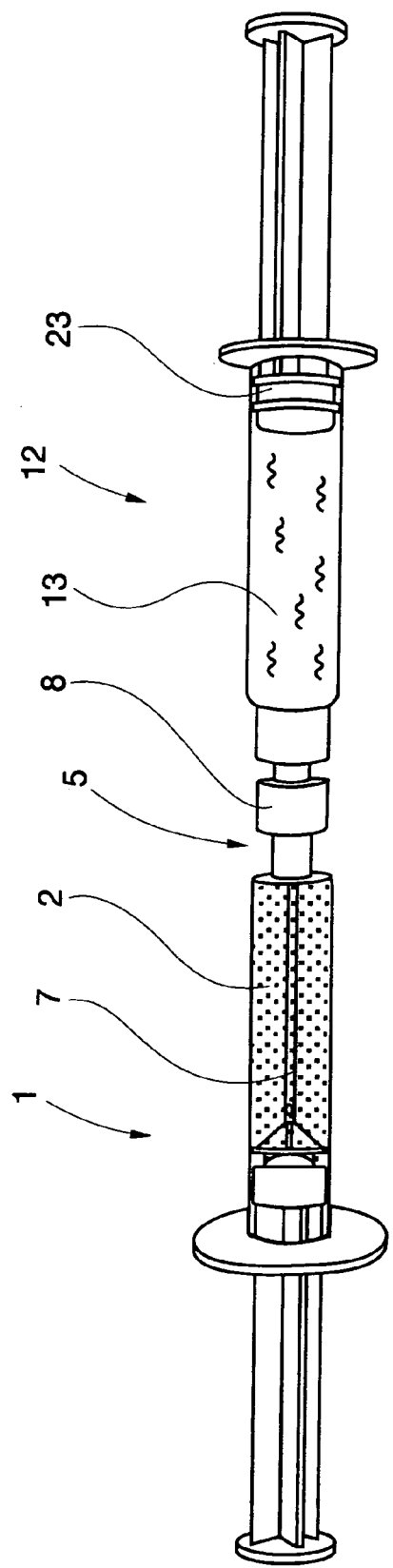
Figure 3C:
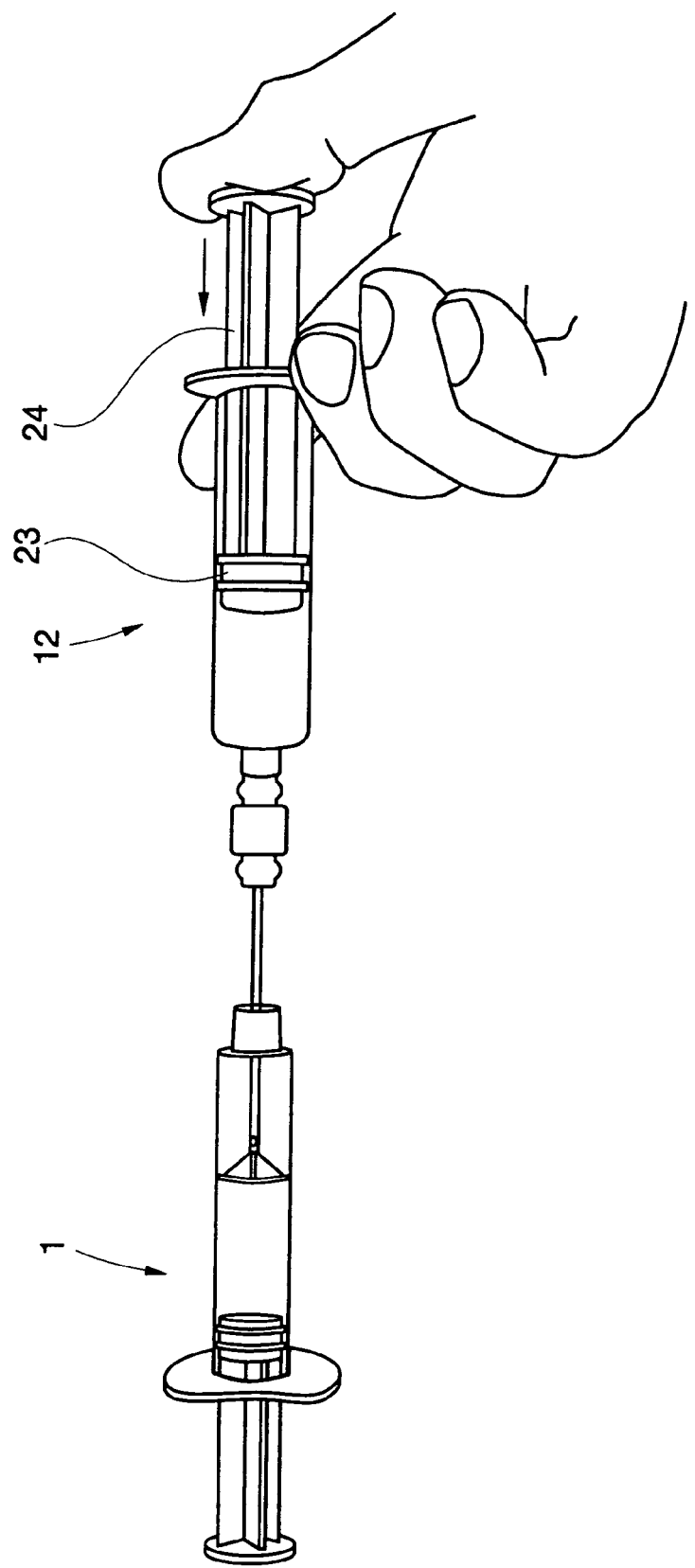

In FIG. 3b is shown the second injection syringe 12 connected or docked to the first injection syringe 1. In FIG. 3c the process is illustrated with feeding of the liquid component 13 from the second 12 to the first 1 injection syringe through pressing-in of the piston 23.

Figure 3D:
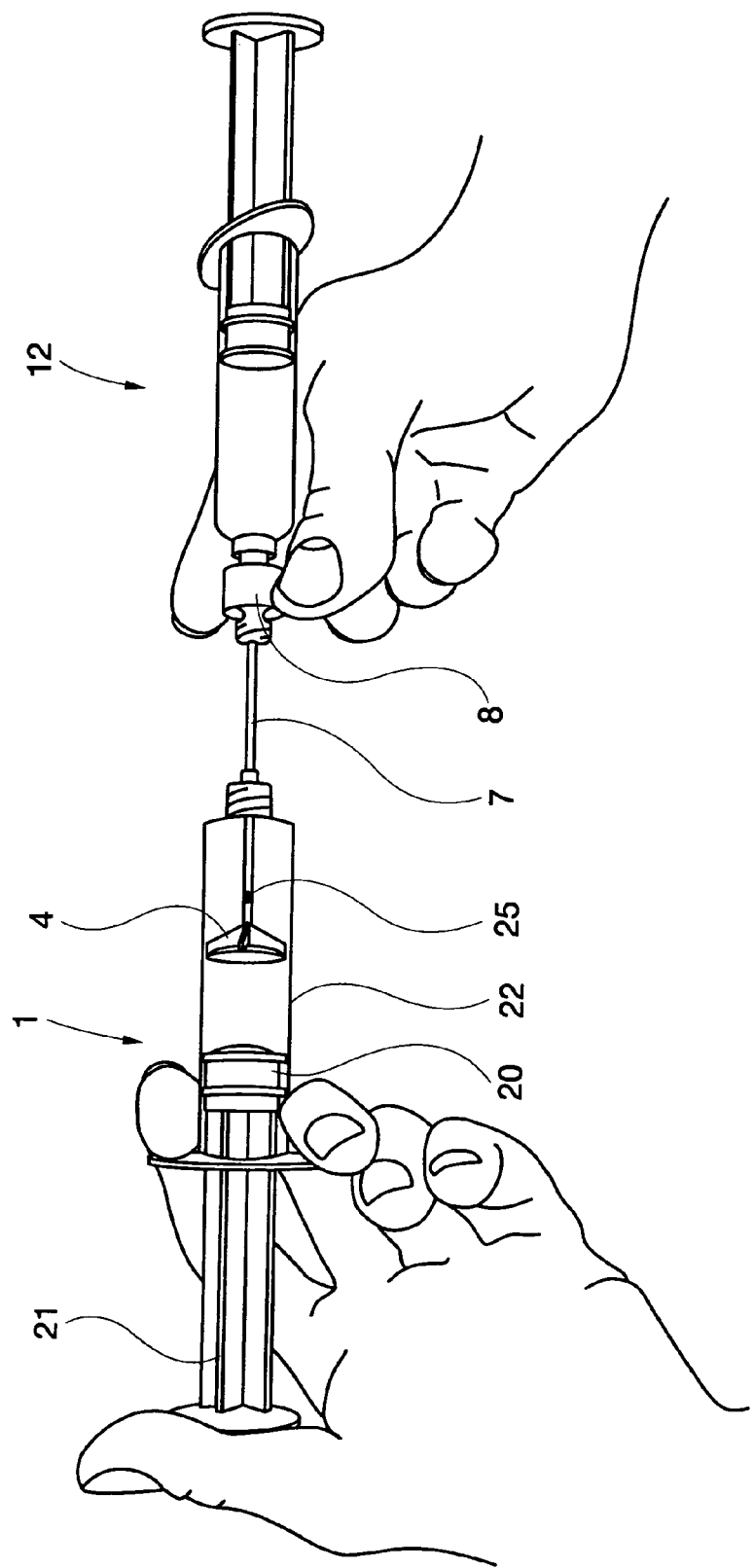

In FIG. 3d is shown the mixing process, wherein the mixing element 4 is rotated at the same time as it is moved in axial direction of the cylinder 22 through actuation of the manoeuvring means 7-8. At the end of this process, the mixture is de-aerated by a minor pressure being applied to the piston 20 over the piston rod 21 in order to create a minor over-pressure inside the cylinder 22 at the same time as the manoeuvring means 7-8 (with connected mixing element 4) is moved in the axial direction. During this important step of the method according to the invention, the completed mixture, which is put somewhat on over-pressure, is effectively de-aerated by gas enclosures in the mixture being "searched" by a mouth 24 to a de-aerating channel, which in this case is the said channel inside the manoeuvring means 7-8. The de-aerating channel can also have more than one mouth 25.

For example, the channel may have two mouths on opposite sides of the manoeuvring means 7-8. Since the second injection syringe 12 is still connected to the first injection syringe 1, captured, in many cases harmful gases, will be received inside the second injection syringe 12 such that they will not reach the operator's respiratory organs.

Figure 3E:
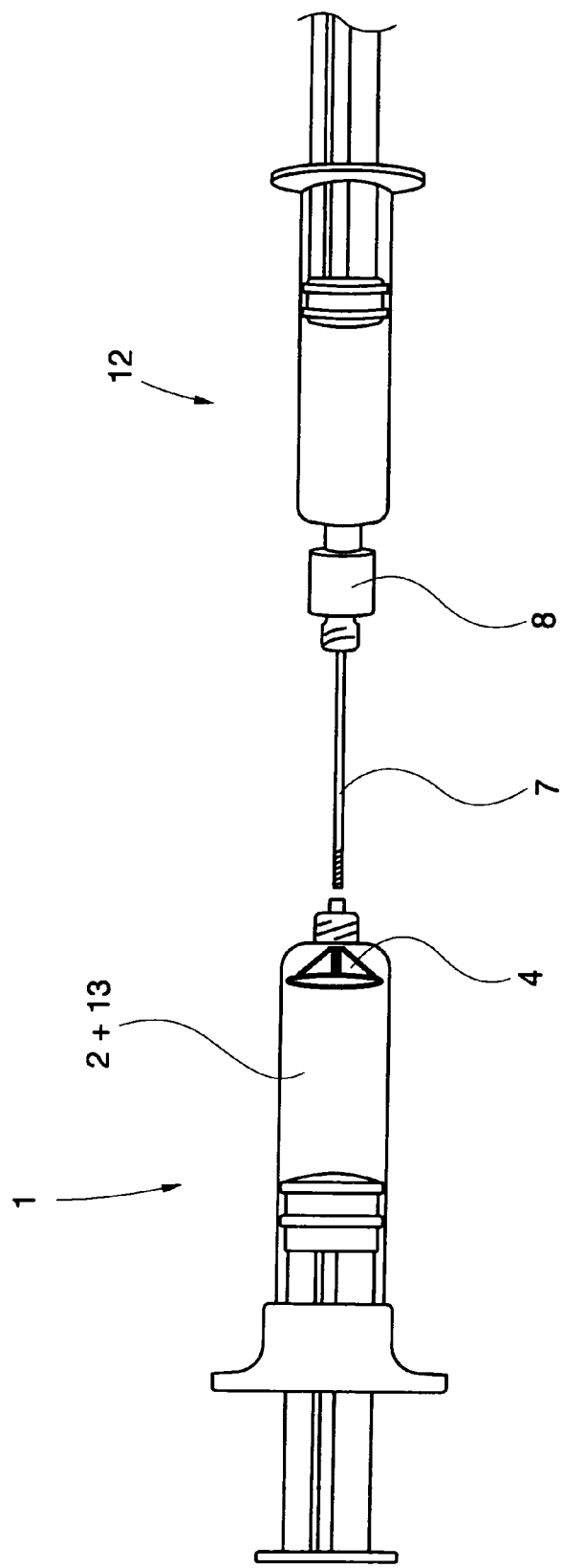

In FIG. 3e is shown that after completed mixing, the manoeuvring means 7-8 for the mixing element 4 is released by simply pulling out the manoeuvring means 7-8 from the first injection syringe 1.

It should been noted that in real life operation, the mixing element 4 can be invisible in some of the sequence steps above because of obscuring (bone cement) mixture. It is, however, for clarity shown throughout the Figures.

Figure 3F:
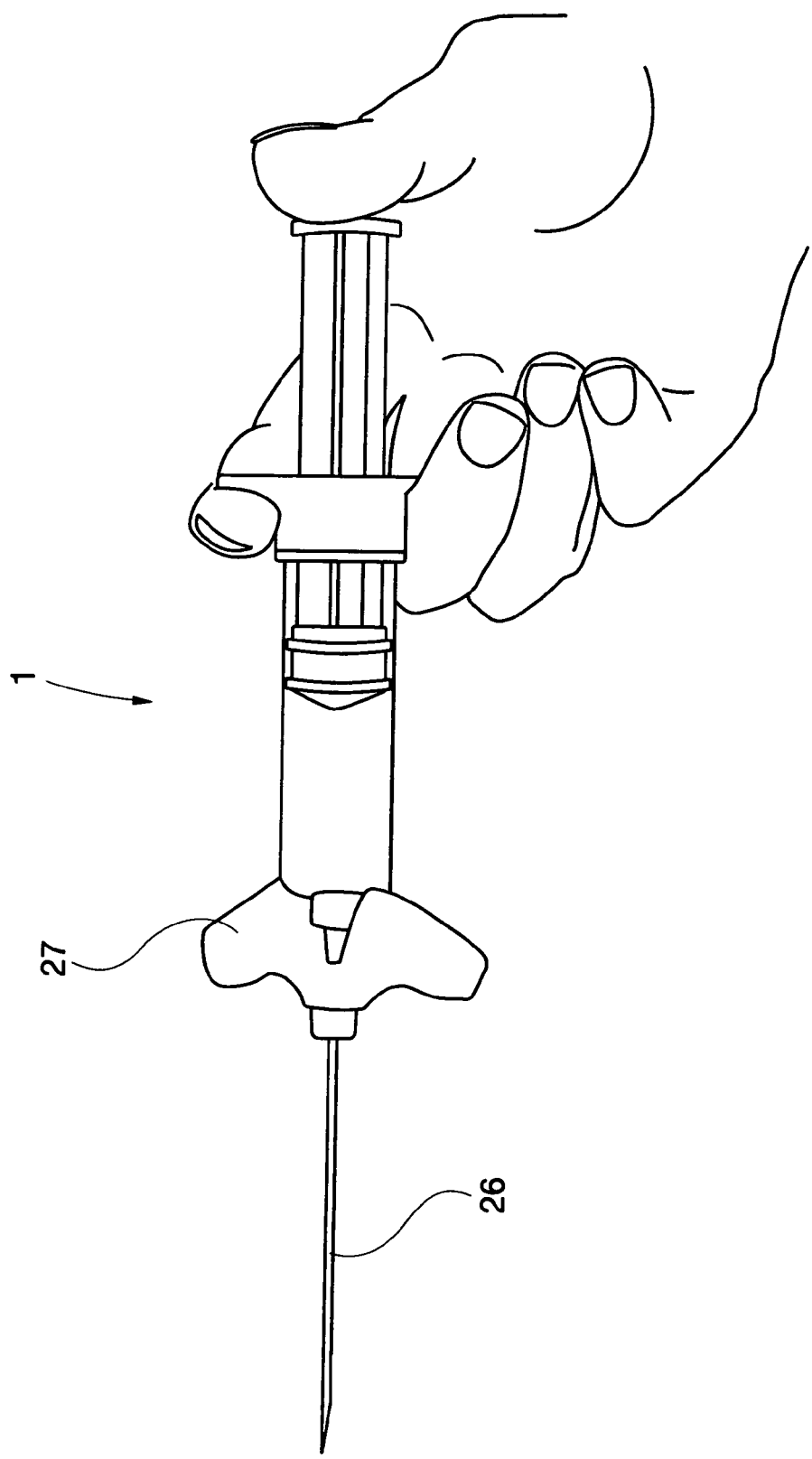

After that, as is shown on FIG. 3f, a chosen injection needle 26 is applied on the first injection syringe 1, in this case with a connected finger grip 27, whereupon the first injection syringe is ready for application of bone cement.

In a second embodiment, which is shown in FIGS. 4-8 the system is somewhat modified. The first injection syringe 1, which is shown in FIG. 4a, is provided with a mixing element 4 with a plurality (e.g., four) of mixing wings 4' in the direction of the outlet of the syringe and, in the opposite direction, a plurality (e.g., four) of pins 4" for providing a good mixing of the components. The detail 4''' is a ring-shaped stabilizing element, which defines axial openings for allowing the mixing components easily to pass through the mixing element 4 during axial movements thereof. In the outlet end of the cylinder 22 is arranged a wiper plate 32, which tightly lies against the tubular portion of the manoeuvring means 7-8 for the purpose of wiping off in particular pulverulent component 2 from this tubular portion when it is pulled in and out of the cylinder 22. Hereby is avoided that the pulverulent material will reach out into the area of the outlet of the first injection syringe 1 and not being part of the mixing. Pulverulent material in this region would also unnecessarily increase friction between the tubular portion of the manoeuvring means 7-8 and the first injection syringe 1 in this area.

Figure 4A:
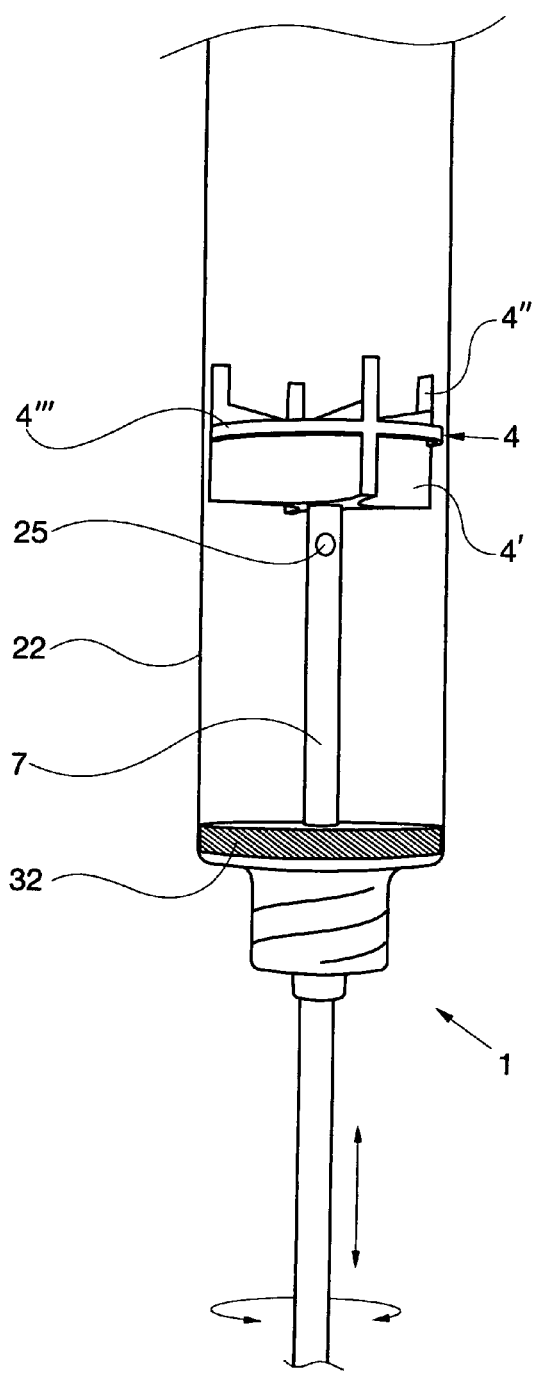
FIGS. 4a-c show a modified first injection syringe in different views.
Figure 4B:
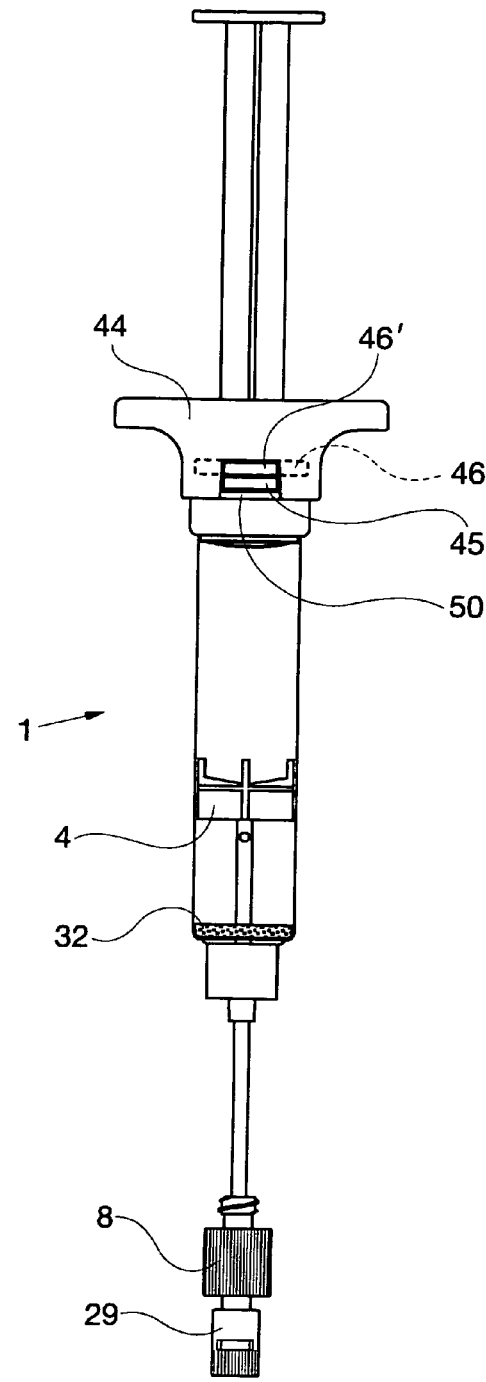

In FIG. 4b is shown at the piston rod side of the first injection syringe 1, a first grip 44, which is rigidly fastenable to the first injection syringe 1, and which has the function of facilitating handling, through a lock washer 46, which can be snapped into a recess in the first grip 44 with radially outwardly extending wings (shown with full lines on the Figure), whereby the locking washer 46 lies in an axial direction against an end flange 45 on the first injection syringe 1.

Figure 4C:
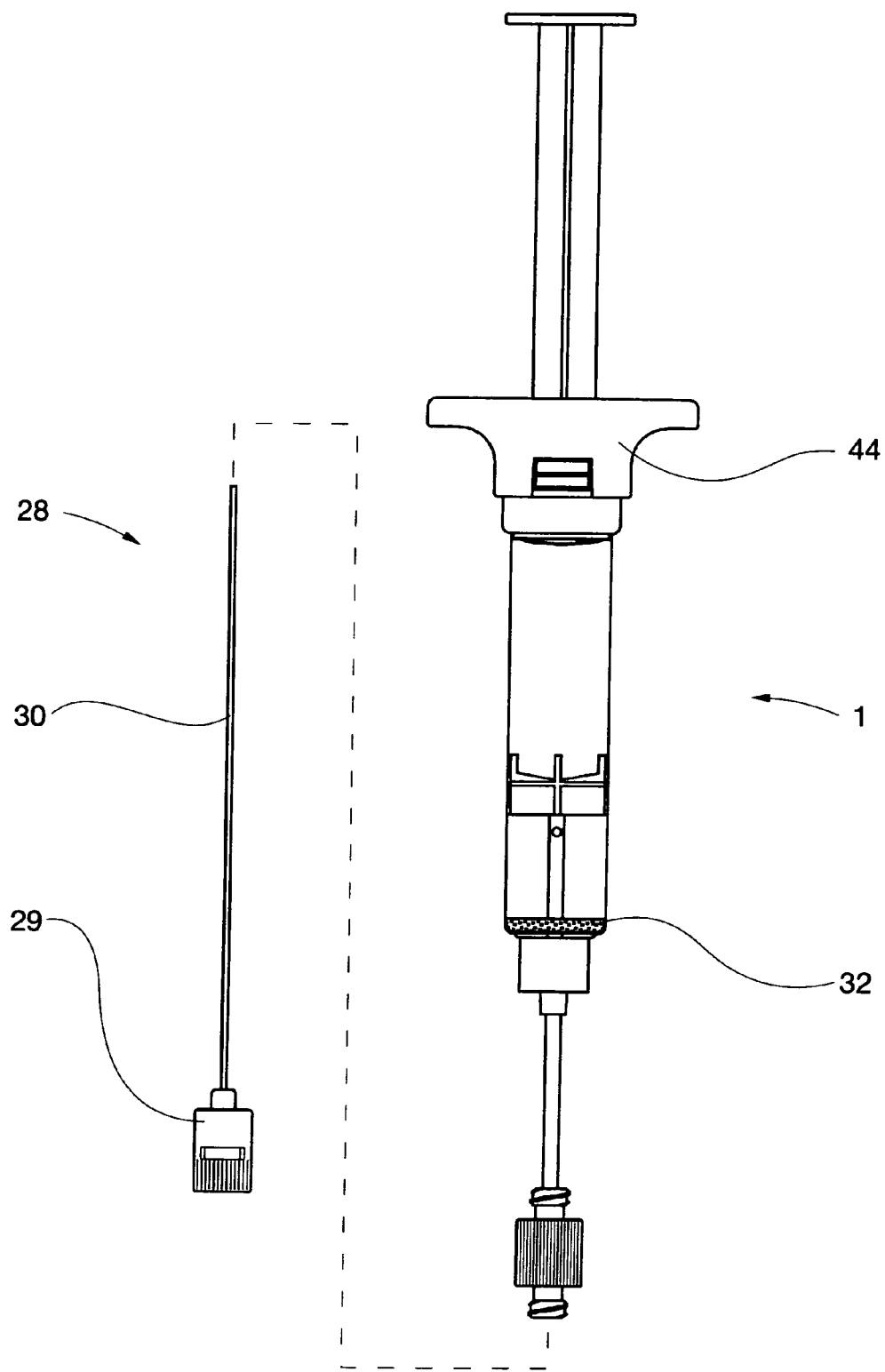

The first grip 44 has a portion at 50 for lying against a second side of this end flange 45. The locking washer 46 further has portions (not shown) which extend radially inwardly inside the section of the cylinder 22, such that they act like a stop and prevent the piston of the first injection syringe 1 from coming out of the cylinder 22. Reference numeral 8 indicates a rotational portion for a manoeuvring means for the mixing element 4. In FIG. 4c is shown the first injection syringe 1 with removed free holding means 28 corresponding to what is described above in respect of the first embodiment.

Figure 5B:
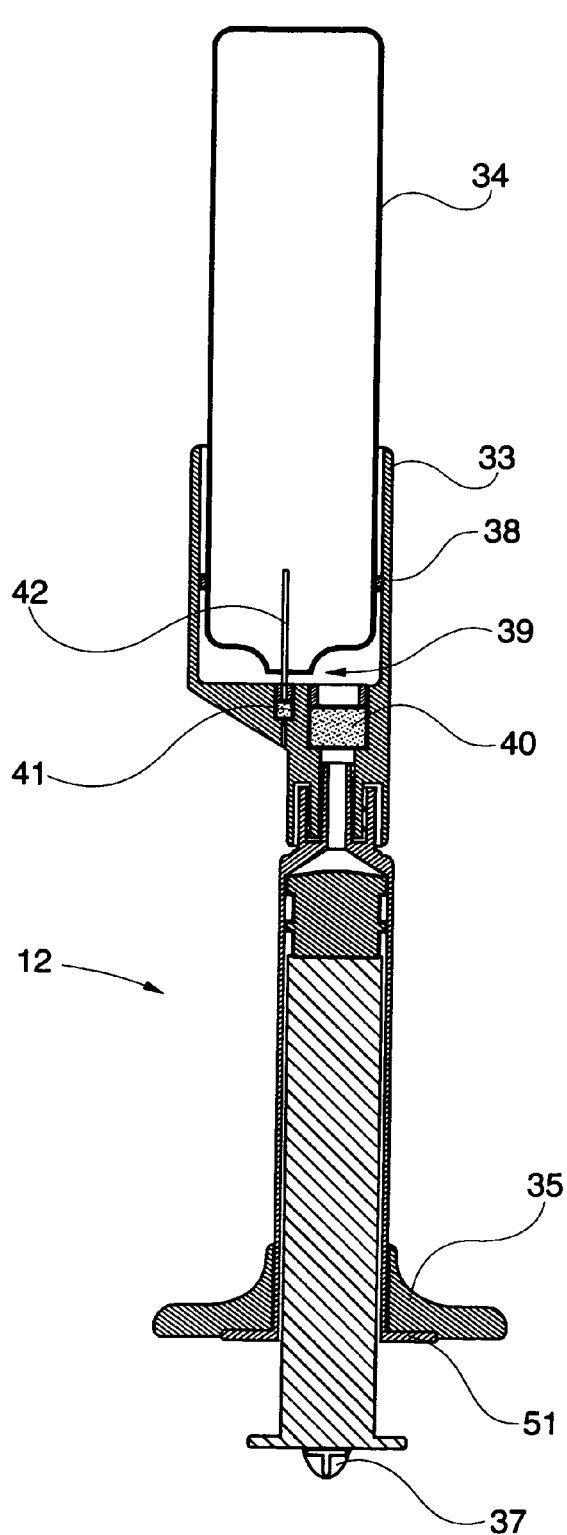
FIGS. 5a and 5b show filling of a modified second injection syringe.
Figure 5A:
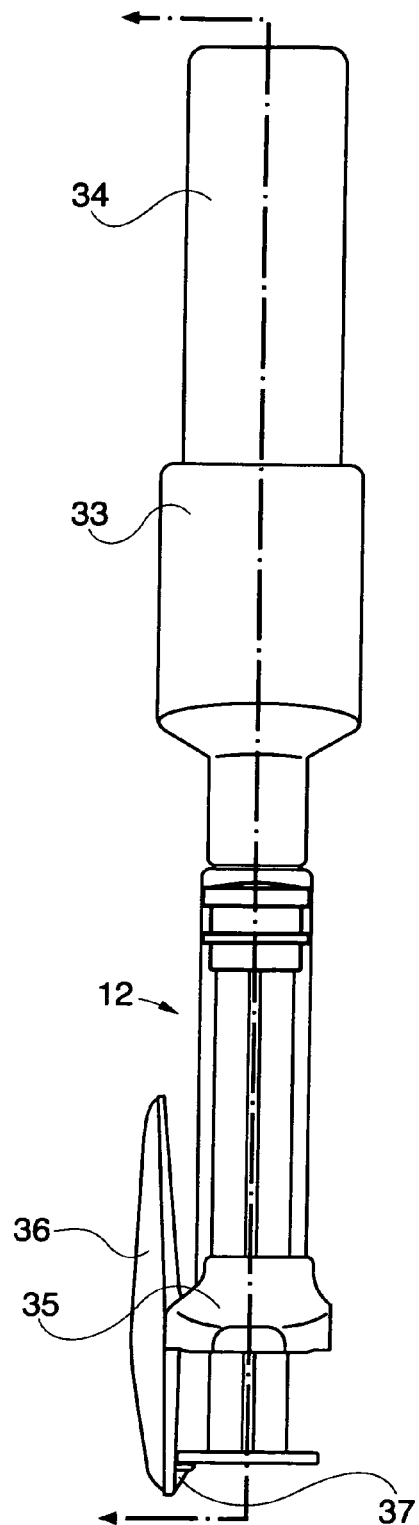

In FIG. 5a is shown an arrangement for filling the second injection syringe 12, wherein it is docked to a first side of an adapter 33, which on its other side, in a vial docking space, is arranged to receive a vial 34 with the liquid component 13. It is further shown on FIG. 5a a second grip 35 for the second injection syringe 12, which grip in an axial direction from an outlet end towards a piston rod end lies against an end flange 51 (FIG. 5b). The second grip 35 has a stop 36, which outermost on the piston end side has a hook means 37 for engagement with an end side of a piston rod which is introducible into the second injection syringe 12. The purpose of stop 36 is to avoid that during later use of the second injection syringe 12, the piston contained therein is moved axially outwardly because of arising over-pressure, which is explained below.

As shown in FIG. 5b, the vial 34 is shown with an opening 39 after braking away of an enclosure end. Reference numeral 38 depicts a sealing/holding ring for ensuring holding of the vial 34 sealingly in position inside the adapter 33. The adapter 33 further has a liquid filter 40 for filtering away impurities such as for example glass particles resulting from breaking of the opening end of the vial 34. Further, the adapter 33 has a venting channel with a venting pipe 42, which is arranged to be introduced somewhat into the vial 34 in its applied position. An air filter 41 is arranged in the venting channel for ensuring sterility of the air provided through the venting channel.

Figure 5C:
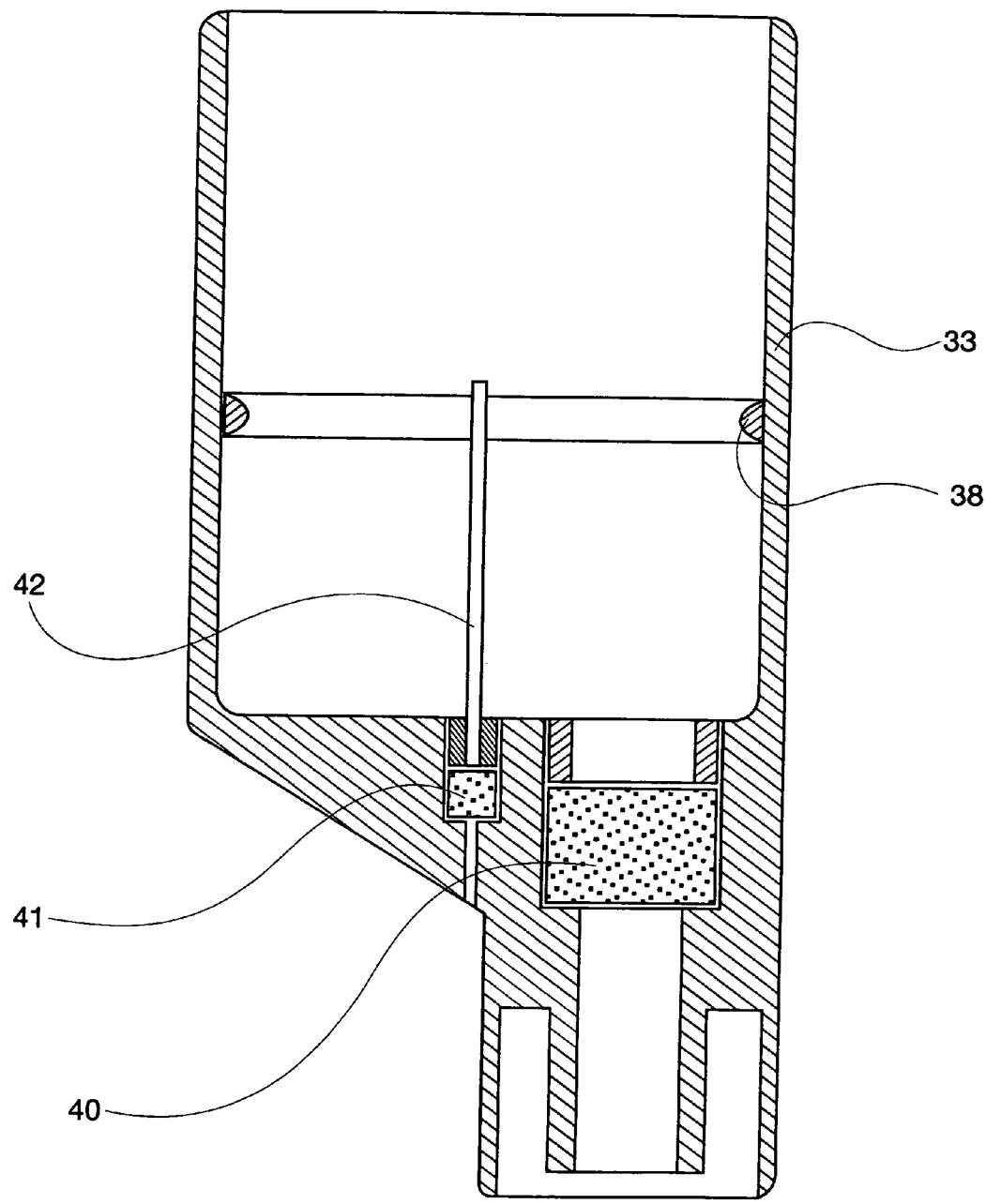
FIG. 5c shows an adapter for filling.

When using the adapter 33, the stop 36 is released such that the second injection syringe 12 can be filled by axial pulling out of the piston in per se known manner until a predetermined amount of the liquid component 13 contained in the vial 34 has been drawn into the second injection syringe 12. Thereupon, the second injection syringe is released from the adapter 33 preferably by screwing out of a threaded connection there between. FIG. 5c shows the adapter 33 more clearly, freed from the vial 34 and from the second injection syringe 12. At the side of docking with a second injection syringe 12, is preferably arranged a thread (not shown) for secure mutual connection of these components.

Figure 6:
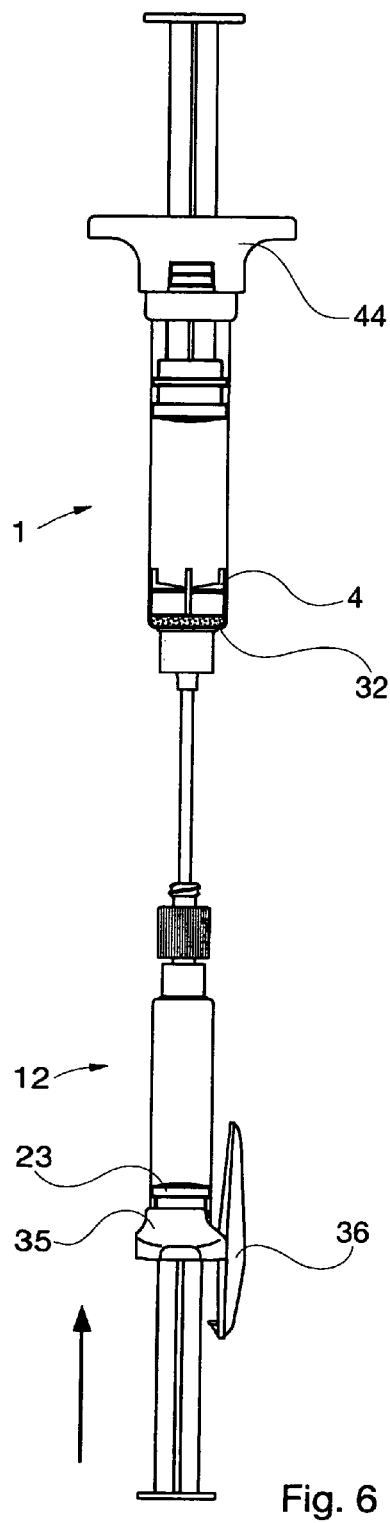
FIG. 6 shows the modified first injection syringe docked to the modified second injection syringe.
Figure 7:
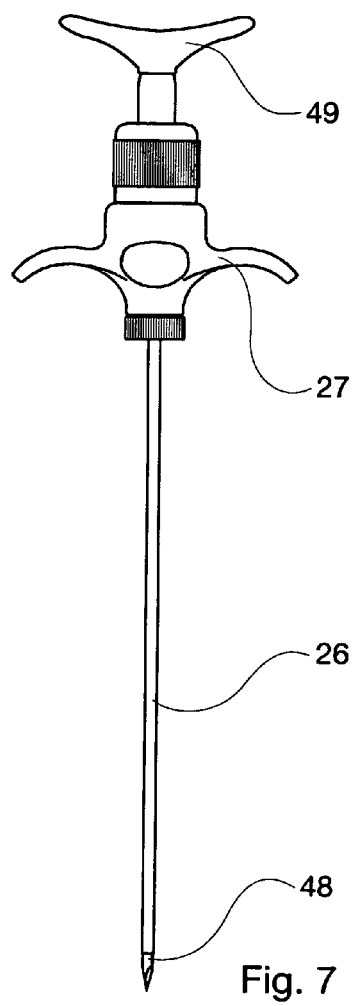
FIG. 7 shows an injection needle for use with a system according to the invention.

In FIG. 6 is shown the two injection syringes 1 and 12 docked to each other prior to feeding of the liquid component 13 from the second injection syringe 12 to the first injection syringe 1. Hereby a piston rod of the second injection syringe 12 is thus pressed axially inwardly until it is locked by the axial stop 36 as is indicated above. During this inward pressure, an over-pressure will result in the connected unit, which would otherwise easily lead to a certain amount of liquid being fed back if the piston 23 would be allowed to move axially from the most inward position. This could give an erroneous mixing relation between the components and inferior properties of the mixture. In FIG. 7 is shown an injection needle unit with an injection needle 26 for driving into bone as for example a vertebra of a patient, into which bone cement is to be injected. The injection needle 26 is shown with an insert point, which has good properties for allowing driving-in of the unit. Reference numeral 27 depicts a finger grip for the unit and reference numeral 49 depicts a press portion, with the aid of which the unit is applied and guided. In connection with the driving-in, the unit could be subjected to minor strikes in a driving direction, which most simply is conducted by removing the press portion 49 and application of strikes against a particular strike receiving element which can be screwed-in to the upper end of the unit.

Figure 8:
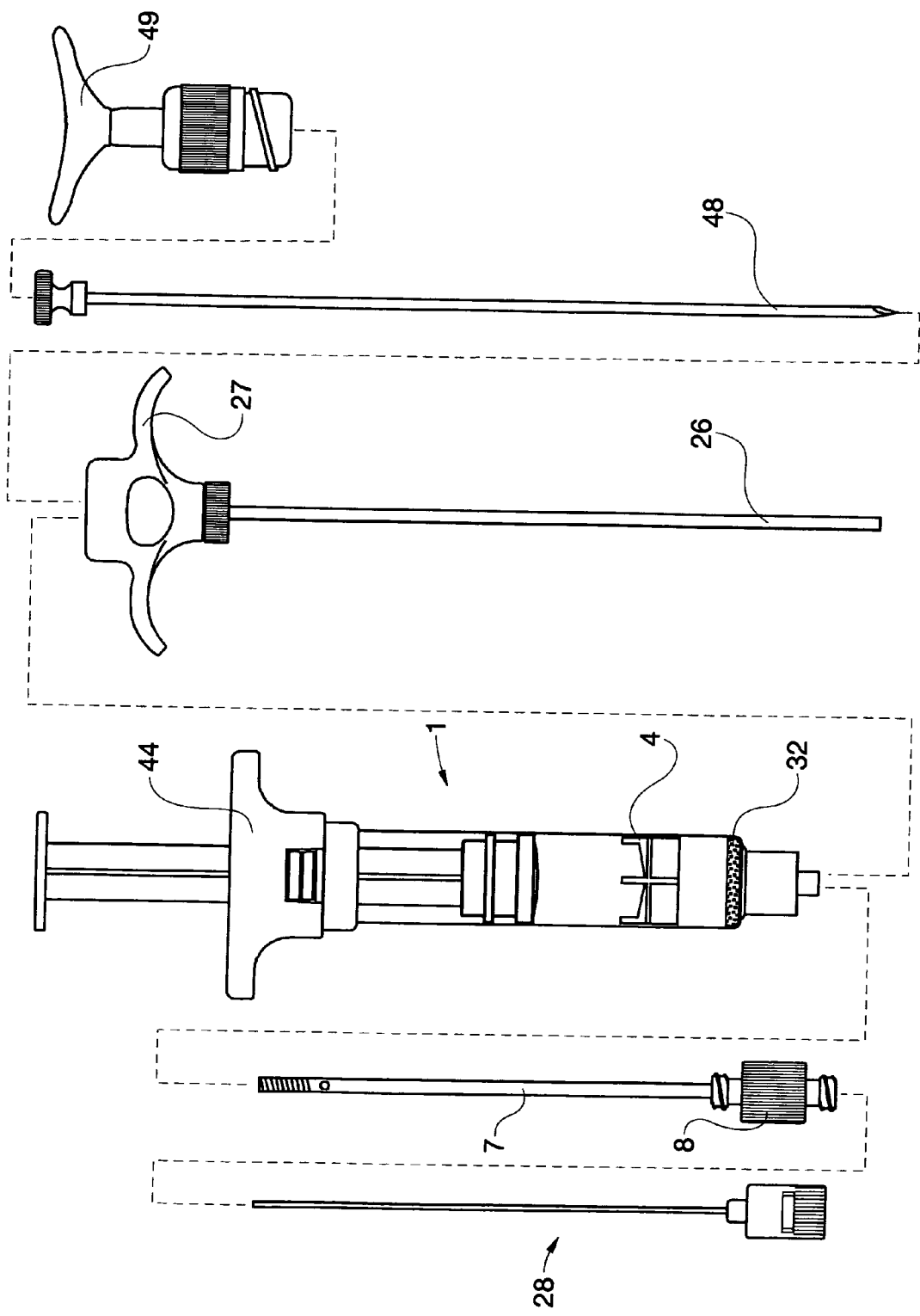
FIG. 8 shows the modified first injection syringe in connection with associated components.

In FIG. 8 is shown the first injection syringe 1 in connection with on the one hand the manoeuvring means 7-8 for the mixing element 4 and the free holding means 28 which is introducible inside, and on the other hand with the injection needle unit with the injection needle 26 and removed insert point 48 as well as removed press portion 49. The manoeuvring means 7-8 is shown with threads for engagement with the mixing element 4 but also other releasable connection can be used such as axial ridges in engagement with the grooves.

The invention can be modified within the scope of the following claims. The filling of the pulverulent component 2 and the liquid component 13 respectively can thus be made differently, even manually, even if automatic filling is preferred. Further, the docking means/engagement means can be constructed differently and gas transferring channels can be arranged differently from what is shown in FIGS. 1a-c. The gas transferring channel means for de-aerating can be separated from the shown manoeuvring means 7-8 for the mixing element, but it is highly preferred that these elements are integrated for simple function and good economy.

The separate reservoir is preferably included, which is described above, in a second piston cylinder arrangement and preferably it is in form of an injection needle. It is, however, also within the scope of the invention, that the separate reservoir is of a different construction, for example a breakable ampoule or without means for pressurizing the liquid component. In one embodiment the separate reservoir, which can be or include such an ampoule, is on one side possible to dock to the first injection syringe 1 and on a second side connected or connectable to a piston cylinder device or any other pressure creating device for driving purposes, whereby can be created an over-pressure such that the liquid component can be introduced into the first cylinder of the first injection syringe 1. In a further embodiment can be provided an under-pressure in the cylinder of the first injection syringe 1, whereby can be initiated that the liquid component 13 can be sucked into this cylinder.

The invention can be used in respect of other mixtures for medical purposes but is preferred in more highly viscous or paste-like mixtures such as bone replacement material or bone cement, even if it is not excluded that the invention is also applicable in more low viscous mixtures with the property of binding air enclosures and therefore should be de-aerated.

For other mixtures that can come into question for the using of a system according to the invention, other sterilizing methods than the above described can come into question. A pulverulent component 2 can for example be sterilized in dry hot atmosphere and a liquid in moist hot atmosphere.

The invention can be modified further and one example of that is that it can be given an indication on when the mixture is completed and as an example also has reached a certain viscosity by using a coupling between the manoeuvring means and the mixing element, which releases from rotation upon reaching a certain viscosity and corresponding rotational resistant of the mixture.

What is claimed is:

1. A system for making an injectable mixture using at least one pulverulent component and at least one liquid component, the system comprising:

an injector including a piston and a cylinder, the cylinder having a proximal end for receiving the piston, a distal end for delivering the injectable mixture, a mixing element manoeuvrable by a user, at least one transfer channel arranged displaceably in the cylinder, and a first engagement element at the distal end of the cylinder, wherein the cylinder contains a measured amount of the at least one pulverulent component; and a reservoir containing a measured amount of the at least one liquid component and having a second engagement element configured for connection with the first engagement element at the distal end of the cylinder to provide for transfer of the at least one liquid component into the cylinder of the injector, wherein, during or following a mixing of the at least one pulverulent component and the at least one liquid component within the cylinder by the mixing element, the at least one transfer channel is axially displaced within the cylinder and through the distal end of the cylinder to remove gas from within the cylinder through one or more apertures in the at least one transfer channel.

2. The system according to claim 1, wherein the reservoir includes a piston and a cylinder.

3. The system according to claim 2, wherein the reservoir has a stop for preventing the piston from moving out of the cylinder.

4. The system according to claim 2, further comprising an adapter with a first side for connection of the reservoir and a second side for connection of a vial containing the at least one liquid component, the adapter configured for transfer of the at least one liquid component from the vial to the reservoir.

5. The system according to claim 4, wherein the adapter is provided with a liquid filter for filtering impurities during the transfer.

6. The system according to claim 4, wherein the adapter has a venting channel with an air filter for ensuring sterility of air brought in through the venting channel during the transfer.

7. The system of claim 2, wherein the reservoir is an injection syringe.

8. The system according to claim 1, wherein the first engagement element is releasable from the distal end of the cylinder of the injector.

9. The system according to claim 1, wherein the mixing element is coupled to and manoeuverable by the at least one transfer channel.

10. The system according to claim 9, wherein the injector includes a wiping plate acting against the at least one transfer channel.

11. The system according to claim 1, wherein the at least one liquid component is transferred into the cylinder via the at least one transfer channel.

12. The system according to claim 1, wherein the mixture is selected from the group consisting of a bone replacement material and bone cement.

13. The system according to claim 1, wherein the injector has a stop for preventing the piston from moving out of the proximal end of the cylinder.

14. The system of claim 1, wherein the injector is an injection syringe.

15. A method for making an injectable mixture using at least one pulverulent component and at least one liquid component, the method comprising:
  supplying a measured amount of the pulverulent component to an injector including a piston and a cylinder, the cylinder having proximal end for receiving the piston, a distal end for delivering the injectable mixture, a mixing element manoeuverable by a user, at least one transfer channel and a first engagement element at the distal end of the cylinder;
  supplying a measured amount of the at least one liquid component to a reservoir, the reservoir including a second engagement element for connection with the first engagement element at the distal end of the cylinder for introduction of the at least one liquid component into the cylinder of the injector;
  connecting the first engagement element with the second engagement element:
  transferring the at least one liquid component to the cylinder of the injector through the connection between the first engagement element with the second engagement element;
  mixing the at least one pulverulent component and the at least one liquid component inside the cylinder of the injector to form the injectable mixture using the mixing element manoeuvrable by a user; and
  during or following the mixing, displacing the at least one transfer channel within the cylinder and through the distal end of the cylinder to remove gas from within the cylinder through one or more apertures in the at least one transfer channel.

16. The method according to claim 15, wherein the reservoir includes a piston and a cylinder.

17. The method according to claim 15, wherein the first engagement element is releasable from the cylinder of the injector.

18. The method according to claim 15, wherein the mixture is selected from the group consisting of a bone replacement material and bone cement.

19. The method according to claim 15, wherein the at least one pulverulent component is sterilized before the mixing using a method selected from the group consisting of sterilizing gas supplied through the at least one transfer channel, radiation and dry heat.

20. The method according to claim 15, wherein the at least one liquid component is sterilized before the mixing using a method selected from the group consisting of aseptic filling over a sterile filter, autoclaving (moist heat) and radiation sterilization.

21. The method according to claim 15, wherein the at least one liquid component is transferred into the reservoir from a vial using an adapter having a reservoir docking space and a vial docking space.

22. The method of claim 15, wherein the injector is an injection syringe.

23. The method of claim 15, wherein the reservoir is an injection syringe.

24. A system for making an injectable paste-like mixture suing at least one pulverulent component and a liquid component, the system comprising:
  a first piston and cylinder arrangement including a piston and a cylinder, the cylinder having an axial extension and containing a measured amount of the at least one pulverulent component;
  a reservoir including a corresponding measured amount of the liquid component; and
  means for sealed transfer of the measured amount of the liquid component to the cylinder for subsequent mixing and injection of the mixture, wherein:
    the first piston and cylinder arrangement is an injection syringe,
    a mixing element being manoeuverable by a user is positioned inside the cylinder,
    at least one gas transferring channel means leading to the cylinder is arranged at the cylinder and displaceable in the cylinder for de-aerating purposes, and
    engagement means are arranged for connecting the first piston and cylinder arrangement to the reservoir during transfer of the measured amount of liquid component.

* * * * *